US009687852B2

(12) United States Patent
Seal et al.

(10) Patent No.: US 9,687,852 B2
(45) Date of Patent: Jun. 27, 2017

(54) SUPPORT FOR BIOCONTAINER BAG

(71) Applicant: Pall Corporation, Port Washington, NY (US)

(72) Inventors: Michael B. Seal, Portsmouth (GB); Paul Clark, Hampshire (GB)

(73) Assignee: PALL CORPORATION, Port Washingon, NY (US)

( * ) Notice: Subject to any disclaimer, the term of this patent is extended or adjusted under 35 U.S.C. 154(b) by 42 days.

(21) Appl. No.: 14/685,748

(22) Filed: Apr. 14, 2015

(65) Prior Publication Data

US 2016/0303567 A1    Oct. 20, 2016

(51) Int. Cl.
| | |
|---|---|
| *B01L 9/00* | (2006.01) |
| *C12M 1/00* | (2006.01) |
| *C12M 3/00* | (2006.01) |
| *B65D 77/06* | (2006.01) |

(52) U.S. Cl.
CPC .............. *B01L 9/00* (2013.01); *C12M 23/14* (2013.01); *C12M 23/48* (2013.01); *B01L 2200/025* (2013.01); *B01L 2200/087* (2013.01); *B01L 2200/18* (2013.01); *B01L 2300/0609* (2013.01); *B01L 2300/0858* (2013.01); *B65D 77/062* (2013.01)

(58) Field of Classification Search
CPC ....... B65D 5/302; B65D 5/46096; B01L 9/00; B01L 2200/18; B01L 2300/0609; B01L 2300/0858; B01L 2200/087
USPC ....... 229/117.14, 198.2; 220/495.06, 495.01, 220/23.91
See application file for complete search history.

(56) References Cited

U.S. PATENT DOCUMENTS

| | | | | |
|---|---|---|---|---|
| 3,114,493 A | * | 12/1963 | Dunkin ................ | B65D 5/0035 206/511 |
| 4,720,020 A | * | 1/1988 | Su .......................... | B65D 19/42 220/1.5 |
| 4,790,029 A | | 12/1988 | LaFleur et al. | |
| 5,316,174 A | * | 5/1994 | Schutz .................. | B29C 70/345 206/386 |
| 5,865,541 A | | 2/1999 | Lafleur | |
| 6,293,418 B1 | | 9/2001 | Ogden et al. | |
| 7,100,786 B2 | | 9/2006 | Smyers | |
| 7,740,212 B2 | | 6/2010 | Austin et al. | |
| 8,858,079 B2 | | 10/2014 | Jiang et al. | |
| 2002/0108950 A1 | | 8/2002 | Moorman et al. | |
| 2010/0316446 A1 | | 12/2010 | Runyon | |
| 2011/0044567 A1 | * | 2/2011 | Barbaroux .............. | B01F 7/163 383/120 |
| 2011/0158037 A1 | | 6/2011 | Bernard et al. | |
| 2011/0198393 A1 | * | 8/2011 | Bates .................. | B65D 5/4608 229/117.14 |

(Continued)

FOREIGN PATENT DOCUMENTS

| | | |
|---|---|---|
| EP | 1 785 360 A1 | 5/2007 |
| EP | 2 103 548 A1 | 9/2009 |

(Continued)

OTHER PUBLICATIONS

Extended European Search Report of European Application No. 16 156 526.2, dated Aug. 10, 2016, 5 pages.

*Primary Examiner* — Stephen Castellano
(74) *Attorney, Agent, or Firm* — Jeremy Jay

(57) ABSTRACT

Supports for biocontainer bags and systems, and methods of using the supports and systems, are disclosed.

12 Claims, 10 Drawing Sheets

(56) References Cited

U.S. PATENT DOCUMENTS

| | | |
|---|---|---|
| 2011/0217767 A1 | 9/2011 | Niazi |
| 2012/0110960 A1 | 5/2012 | Baud et al. |
| 2013/0161229 A1 | 6/2013 | Barbaroux et al. |
| 2013/0193153 A1 | 8/2013 | Baltz et al. |
| 2014/0048546 A1* | 2/2014 | Kennis .................. B65D 33/02 220/666 |

FOREIGN PATENT DOCUMENTS

| | | |
|---|---|---|
| EP | 2 326 412 B1 | 5/2012 |
| EP | 2 607 474 A1 | 6/2013 |
| WO | WO 2006/119513 A1 | 11/2006 |
| WO | WO 2013/171340 A2 | 11/2013 |

* cited by examiner

SUPPORT FOR BIOCONTAINER BAG

BACKGROUND OF THE INVENTION

Biocontainer bags can be packaged with tubing and connectors. Some biocontainer bags are large (e.g., about 1000 L or more) and/or unwieldy to handle, transport, and/or set up.

The present invention provides for ameliorating at least some of the disadvantages of the prior art. These and other advantages of the present invention will be apparent from the description as set forth below.

BRIEF SUMMARY OF THE INVENTION

An embodiment of the invention provides a support for a biocontainer bag including an impeller to be placed in a tote comprising (a) a base plate having opposing sides, a front end and a rear end, and including a generally centrally located first opening; and an offset second opening located near the front end; the first opening having a first diameter; the offset second opening having a second diameter, the second diameter being smaller than the first diameter; the base plate further comprising a notch at the rear end, wherein the notch allows alignment with a tote; wherein the base plate, when placed in the tote, has a horizontal axis providing a high point and a low point, the low point being located at the offset second opening; and, (b) first and second opposing side walls, hingedly connected to respective opposing sides of the base plate, each side wall having an upper portion and a lower portion, and a horizontally arranged hinge between the upper portion and the lower portion, and including at least one opening suitable for grasping the side wall and/or including a strap for carrying the support while transporting the biocontainer bag to and/or from the tote.

BRIEF DESCRIPTION OF THE SEVERAL VIEWS OF THE DRAWING(S)

FIG. 1 is a top view of a support according to an embodiment of the present invention, comprising a base plate having a generally located first opening, and an offset second opening; first and second opposing side walls; and a front wall; wherein the support has been laid flat, and the support further comprises first and second straps, respectively attached to the first and second opposing side walls.

DETAILED DESCRIPTION OF THE INVENTION

Figure 1:
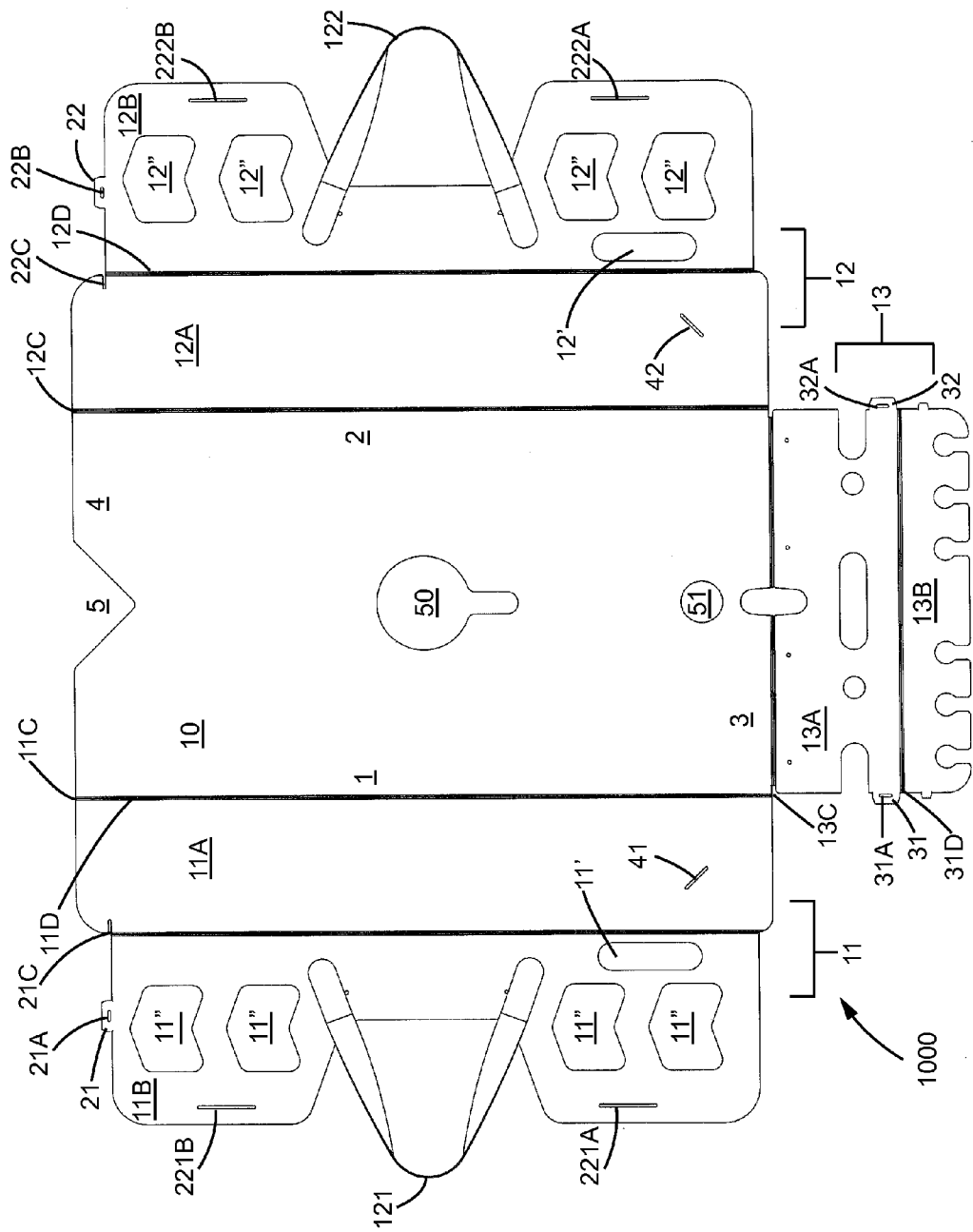
Figure 2:
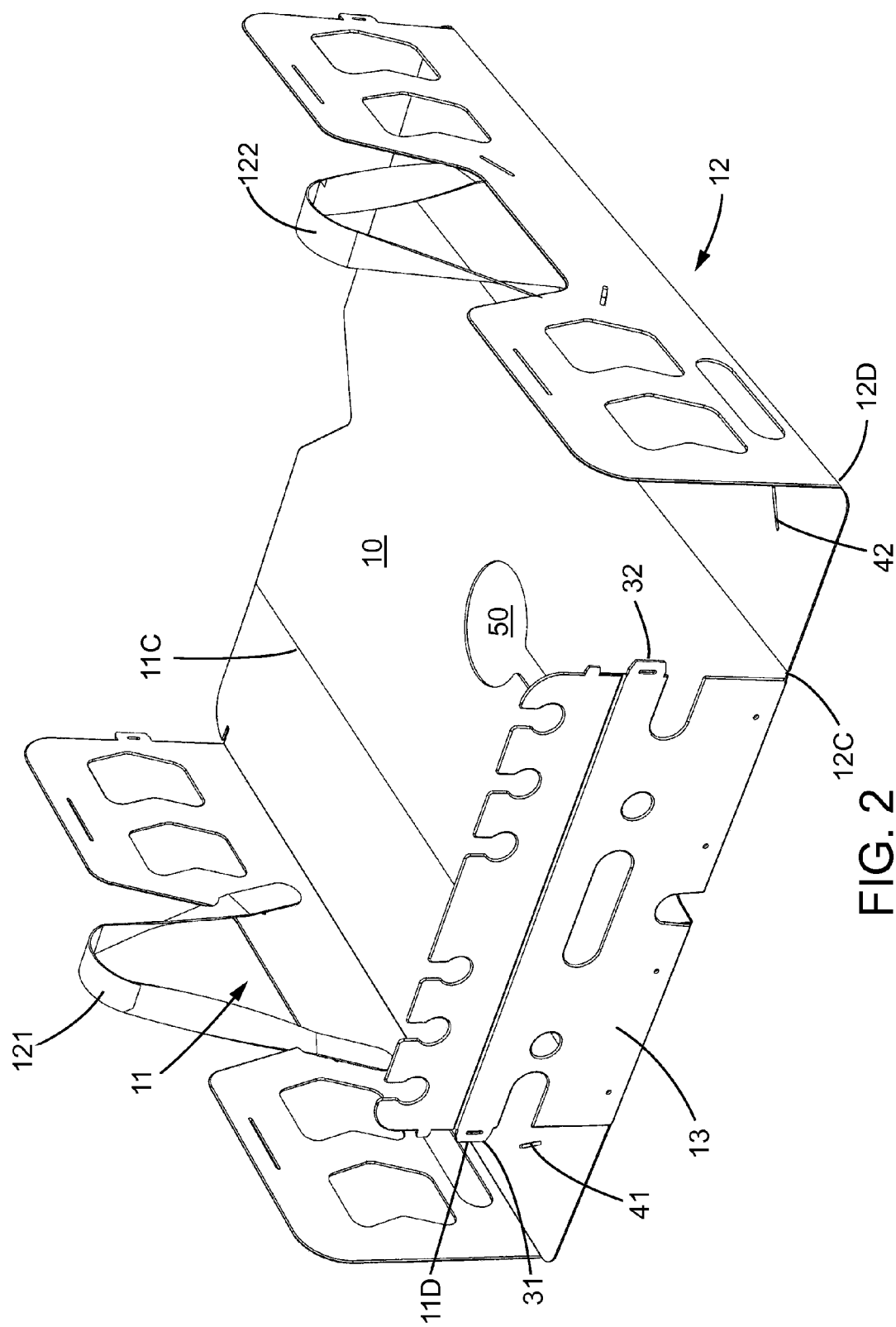
FIG. 2 is a perspective view of the support shown in FIG. 1, showing a hinged connection between the front wall and the base plate, and hinged connections between upper and lower portions of the opposing side walls.

In accordance with an embodiment of the present invention, a support for a biocontainer bag including an impeller to be placed in a tote is provided, comprising (a) a base plate having opposing sides, a front end and a rear end, and including a generally centrally located first opening; and an offset second opening located near the front end; the first opening having a first diameter; the offset second opening having a second diameter, the second diameter being less than the first diameter; the base plate further comprising a notch at the rear end, wherein the notch allows alignment with a tote; wherein the base plate, when placed in the tote, has a horizontal axis providing a high point and a low point, the low point being located at the offset second opening; and, (b) first and second opposing side walls, hingedly connected to respective opposing sides of the base plate, each side wall having an upper portion and a lower portion, and a horizontally arranged hinge between the upper portion and the lower portion, and including at least one opening suitable for grasping the side wall and/or including a strap for carrying the support while transporting the biocontainer bag to and/or from the tote.

In a preferred embodiment, the support further comprises a front wall, hingedly connected to the front end of the base plate. If desired, the front wall has an upper portion and a lower portion, and a horizontally arranged hinge between the upper portion and the lower portion. The front wall may have tabs, and the side walls may each have a receiving slot, wherein the tabs on the front wall are insertable into the receiving slots to temporarily engage the front wall and side walls together in place. Typically, the front wall has a plurality of slots and/or openings for accommodating biocontainer bag tubing, probe supports, and/or ports.

In a preferred embodiment of the support, the side walls and/or the front wall are attached to the base plate as an integral structure.

Typically, the support further comprises first and second straps, respectively attached to the first and second opposing side walls.

In an embodiment, the support is suitable for supporting a biocontainer tube management system comprising a biocontainer bag and a tube support, wherein the upper portions of each of the first and second opposing side walls each include at least two slots for engaging the tube support.

In another embodiment, a method for transporting a biocontainer bag is provided, the method comprising placing the biocontainer bag on the base plate of the support, moving at least the lower portions of the first and second opposing walls to substantially vertical positions, and transporting the biocontainer to a desired location. In some embodiments, the method further comprises moving the upper portions inwardly via the horizontally arranged hinge.

Embodiments of the method can further comprise, before transporting the biocontainer bag to a desired location, inserting the tabs on the front wall into the receiving slots of the side walls, and temporarily locking the front wall and side walls together.

In a preferred embodiment, the method further comprises placing the support in the tote, wherein a baffle of the tote is located in the notch in the base plate.

Advantageously, biocontainer bags can be more easily transported before and after use, and the footprint of the bags can be reduced. Additionally, or alternatively, tubing can be accommodated by a portion of the support, while minimizing the potential for creasing or folding the tubing.

Figure 8:
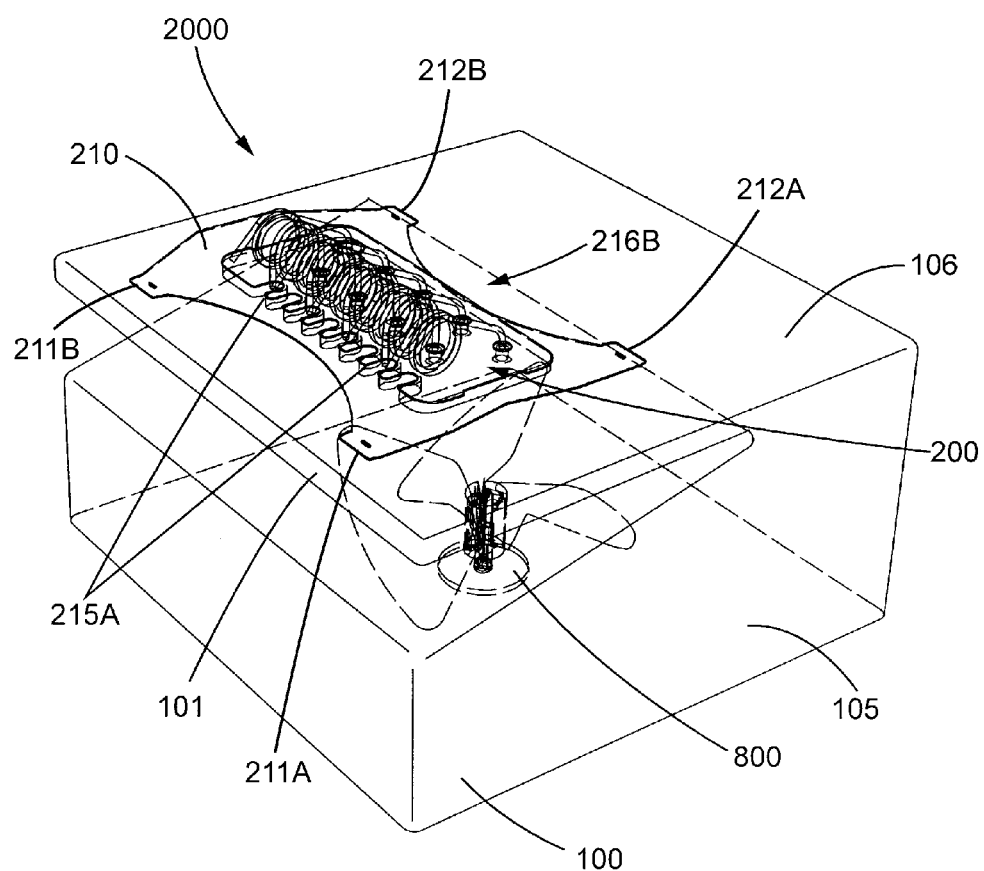
FIG. 8 is a view of an illustrative biocontainer tube management system, comprising a partially inflated biocontainer bag (including an impeller) and a tube support, suitable for use with a support according to an embodiment of the invention.

Embodiments of the invention are suitable for use in supporting and/or transporting a variety of biocontainer bags (or bioreactor bags or bioprocessing containers) having any volume, and are especially suitable for bags with larger volumes, e.g., having a volume of at least about 500 L, or at least about 1000 L, or greater. A bioreactor bag can have any suitable form (e.g., cylindrical (having, for example, a single continuous side wall), square, or rectangular), and in FIG. 8 is illustrated as having a generally rectangular cuboid form with a plurality of side walls. Preferably, the biocontainer bags are flexible (e.g., made including plastic material).

Each of the components of the invention will now be described in more detail below, wherein like components have like reference numbers.

FIG. 1 shows an embodiment of the support 1000, laid flat. The illustrated support comprises a base plate 10, having a opposing sides 1, 2, a front end 3, a rear end 4, and including a generally centrally located first opening 50, and an offset second opening 51 located near the front end. The base plate also has a notch 5 at the rear end (e.g., for better locating the support in the tote and fitting a baffle of the tote in the notch). First and second opposing side walls 11, 12 are connected to respective opposing sides of the base plate via hinges 11C, 12C. Each side wall has a lower portion 11A, 12A and an upper portion 11B, 12B, with a horizontally arranged hinge 11D, 12D between the upper and lower portions.

The illustrated embodiment also includes a front wall 13, connected to the front end of the plate via hinge 13C. The illustrated front wall has a lower portion 13A and an upper portion 13B, with a horizontally arranged hinge 13D between the upper and lower portions.

The surfaces of the walls and base plate that will contact the biocontainer bag are shown as smooth, but can include, for example, ribs, e.g., for assisting in drainage of the bag.

Preferably, the side walls and front walls are attached to the base plate integrally via the hinges (e.g., using a "living hinge," made from the same material as the base plate and walls), rather than separately attached via additional structures such as bolts, screws, or rivets. Similarly, the hinges connecting the upper and lower portions of the walls are preferably living hinges. A variety of materials are suitable for use in providing the walls and base plate, e.g., providing a suitably rigid support. One example of a suitable material is high density polyethylene (HDPE).

Figure 3:
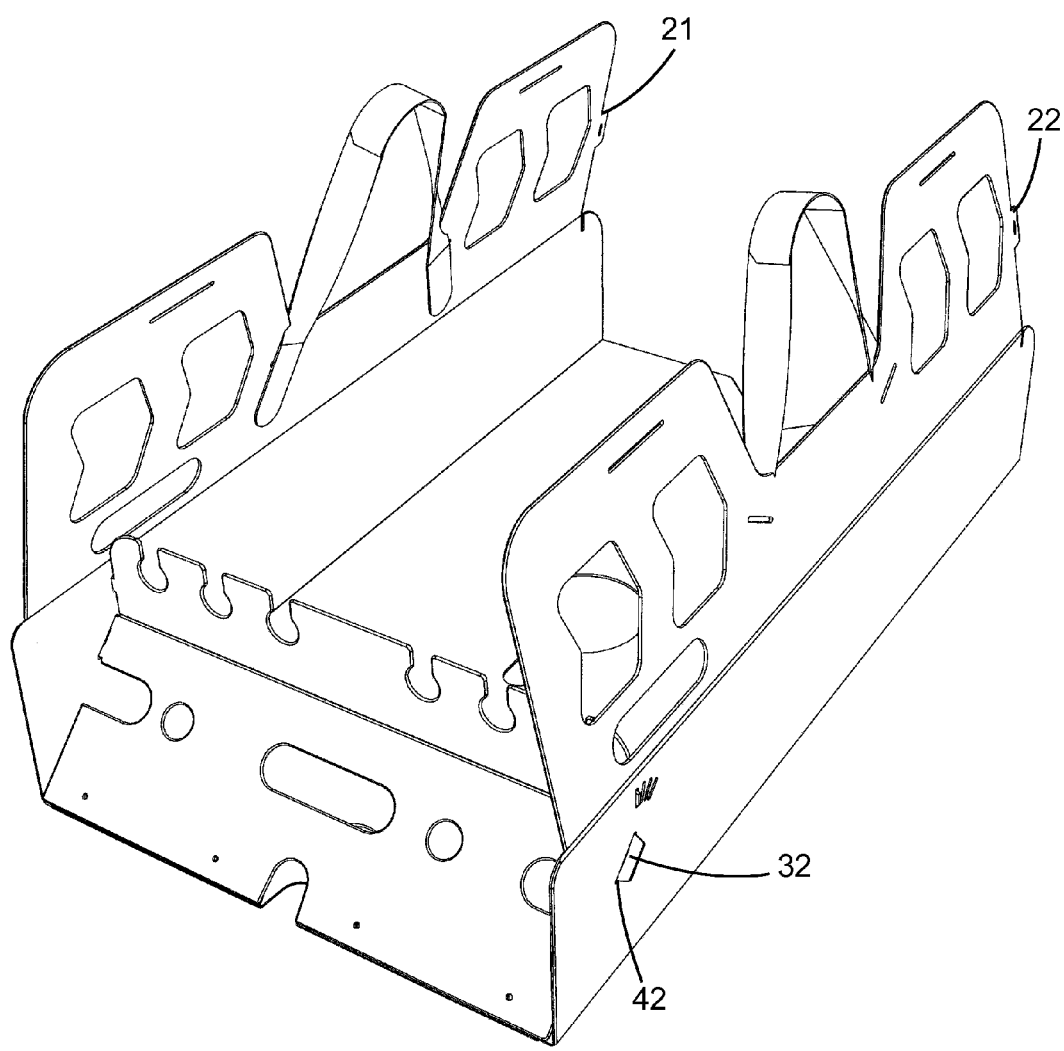
FIG. 3 is a partially assembled view of the support shown in FIG. 1, after tabs on the front wall are engaged with slots on the side walls, also showing hinged connections between the lower portions of the side walls and the base plate, and a hinged connection between upper and lower portions of the front wall.
Figure 5:
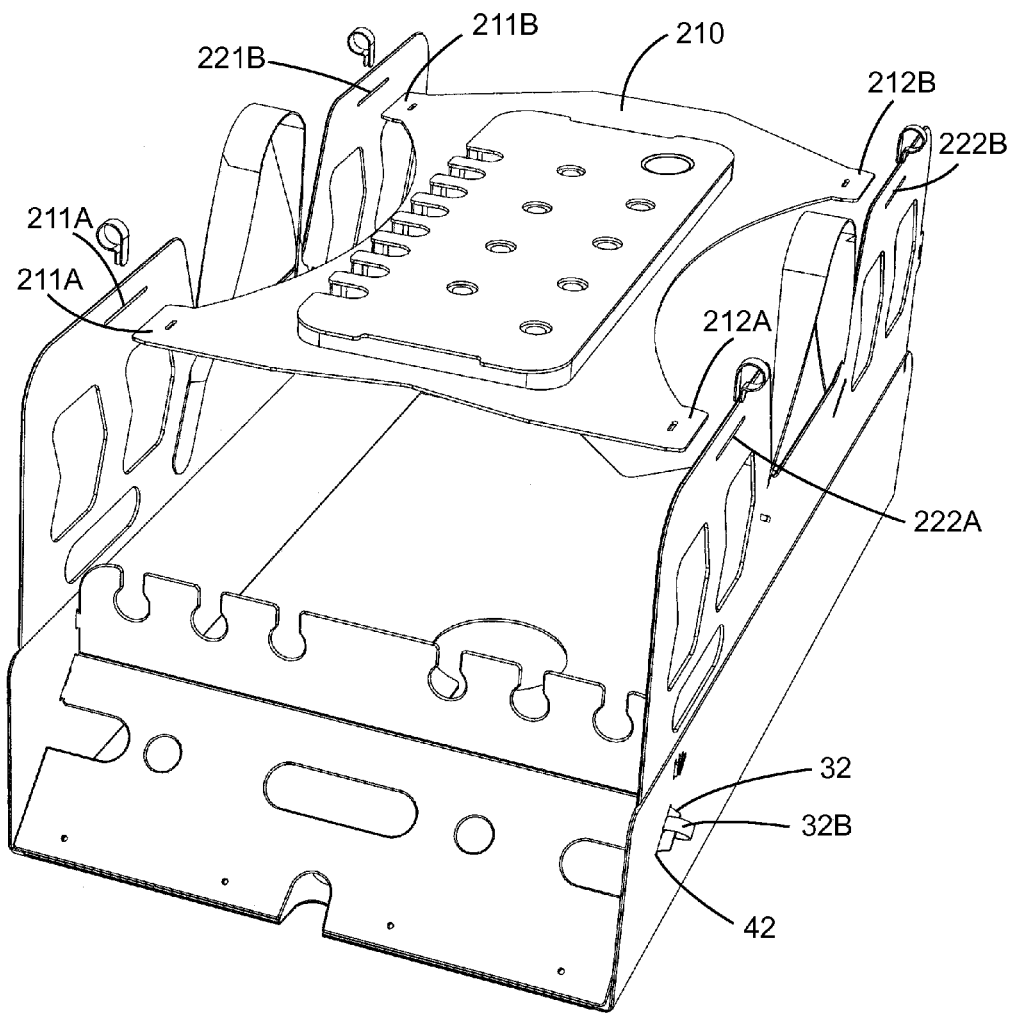
FIG. 5 is a view of a partially assembled support for use with a biocontainer tube management system comprising a biocontainer bag and a tube support, also showing the tube support of the tube management system.

Preferably, and as shown in FIG. 1, the front wall 13 has tabs 31, 32 on opposing sides of the front wall, and the side walls 11, 12 have receiving slots 41, 42, respectively, wherein the tabs are insertable into the receiving slots to temporarily engage the front wall and side walls together in place (e.g., as shown in FIG. 3). If desired, the tabs 31, 32 can also include slots 31A and 32A, allowing retainers (e.g., straps, clips, or flexible ties) to be placed in the slots to more securely (but temporarily, if desired), lock the front wall and side walls together (e.g., as shown in FIGS. 5 and 6, showing retainer 32B).

Figure 6:
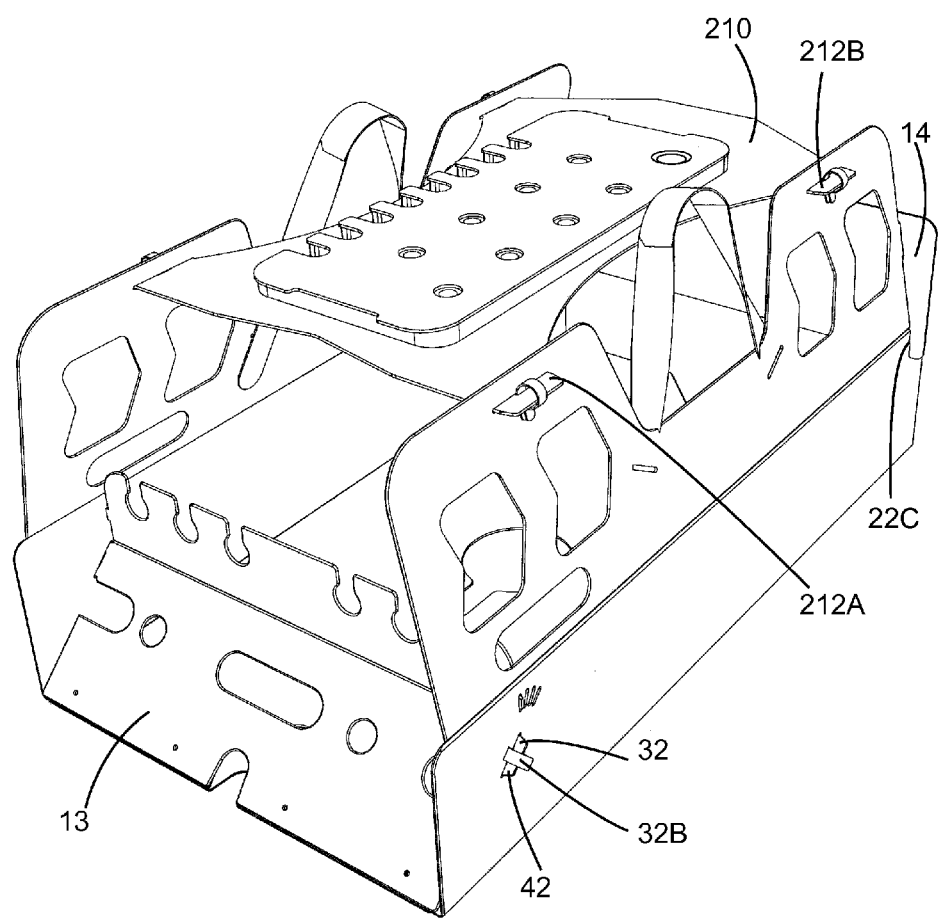
FIG. 6 is a front perspective view of the assembled support as shown in FIG. 5, wherein the tube support of the biocontainer tube management system is retained in the upper portions of the opposing side walls.
Figure 7:
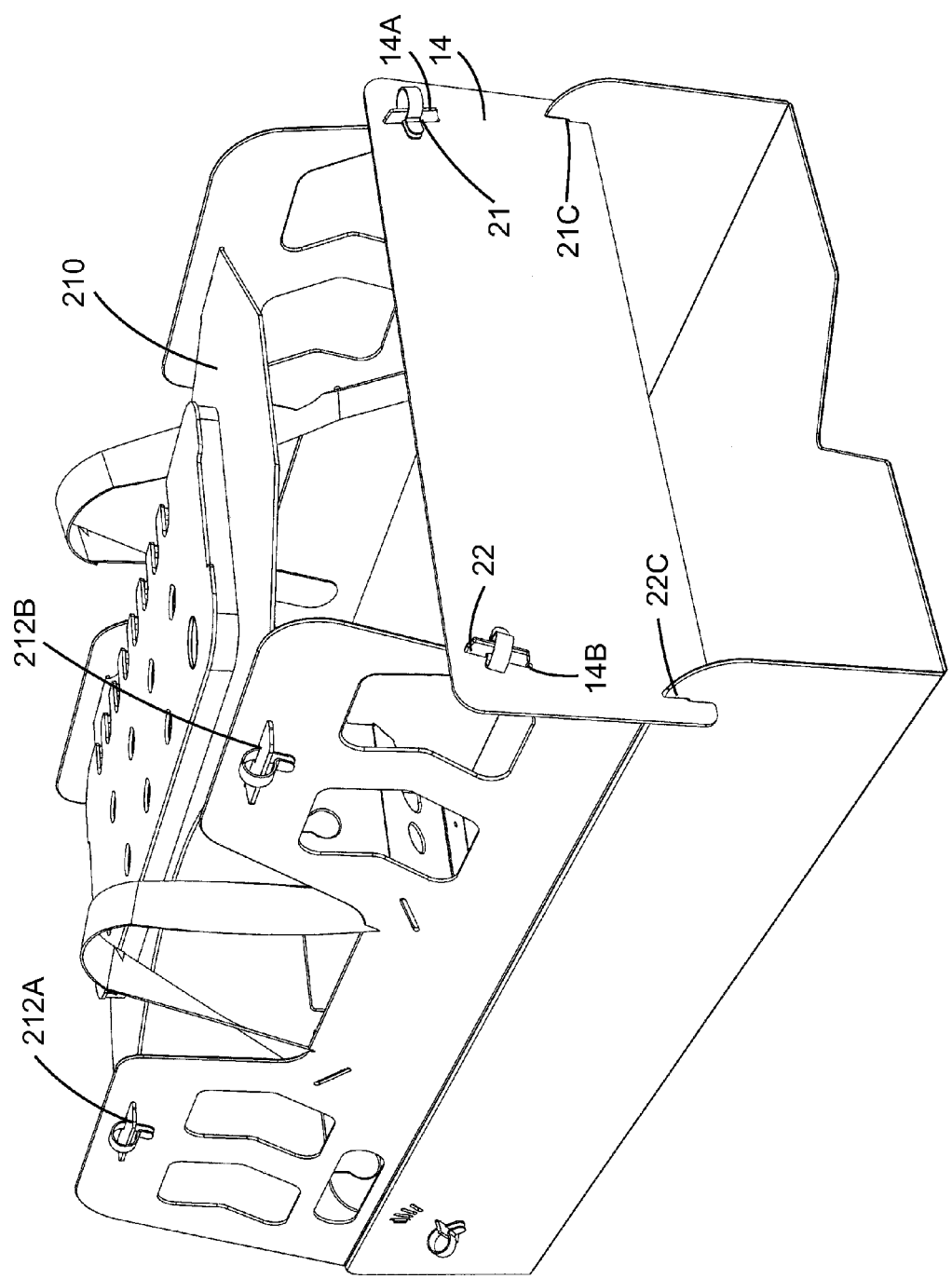
FIG. 7 is a rear perspective view of the assembled support as shown in FIG. 6, also showing a rear retaining wall, engaged with both the upper and lower portions of the opposing side walls.

Optionally, as shown in FIG. 1, the side walls 11, 12 can include tabs 21, 22, and slots 21C, 22C, respectively, e.g., wherein the support further comprises a rear wall 14 that engages with the slots 21C, 22C, and the rear wall includes slots 14A, 14B, such that tabs 21, 22 engage with slots 14A, 14B, respectively (e.g., as shown in FIGS. 6 and 7). If desired, the tabs 21, 22, can also include slots 21A and 22A, allowing retainers to be placed in the slots to more securely (but temporarily, if desired), lock the rear wall and side walls together (e.g., as shown in FIG. 7).

In the embodiment illustrated in FIG. 1, the support also includes straps 121, 122, attached to side walls 11 and 12, respectively. Optionally, and as shown in FIG. 1, the each side wall also include includes at least one opening 11' and 12' (illustrated as having an oval shape, though a variety of shapes are suitable). The use of straps and/or openings can be advantageous for transporting the biocontainer to and/or from the tote, e.g., the operator can grasp the side walls via the openings and/or carry the support via the straps.

In the embodiment illustrated in FIG. 1, side walls 11 and 12 each also include at least one additional openings, shown as a plurality of "chevron-shaped" openings 11", 12". Additional openings can be advantageous for providing open areas allowing single-use biocontainer bags to contact a side of the tote to maximize heat transfer. If such additional openings are included, they can have a variety of shapes, and can be of any suitable number. The use of a chevron shape can be desirable for providing the operator with a directional indication for loading into the tote.

As will be described in more detail below with respect to FIGS. 5-7 and 9, first and second sidewalls 11, 12 can include respective sidewall slots 221A, 221B, 222A, and 222B.

Embodiments of the support are particularly useful for transporting biocontainer bag sets including tubing, probe supports, and/or ports. For example, front wall portions 13A and 13B shown in FIG. 1 have a plurality of slots and openings for supporting bag set tubing and/or to allow probe supports and/or ports attached to the biocontainer to extend through the wall to reduce damage while transporting the biocontainer bag set. Additionally, or alternatively, and using, for example, FIG. 3 for reference, the hinge 13D between upper and lower portions 13A and 13B allows the portions to be oriented differently, creating a "compartment" for tubing arranged at the front end 3 of the base plate and in the area created at the interior of portion 13A, thus reducing the potential for creasing or folding the tubing, while portion 13B can be arranged more vertically for better support of ports and/or tubing extending through the slots in portion 13B (as shown in, for example, FIGS. 9 and 10, wherein slots in portion 13B, and openings in portion 13A support biocontainer bag ports).

Using FIGS. 1-3, and 10, for reference, the use of the various hinges allows the operator to, after placing a biocontainer bag containing an impeller on the base plate, such that the impeller is located above first opening 50 (the first opening having a first diameter allowing the lower portion of an impeller housing to pass through the opening (as shown in more detail in FIG. 10)), and the drain port in the biocontainer bag is located over the second opening 51 (the second opening having a second diameter that is less than the first diameter, the second diameter being sufficient for accommodating the drain port (as shown in more detail in FIG. 10)), fold the sides of the support around the biocontainer, for ease of handling and transport. Once the sides are suitable arranged, the operator can grasp the support, e.g., using holes in the side walls and/or the straps, and transport the biocontainer as desired, e.g., to and from the tote.

Figure 4:
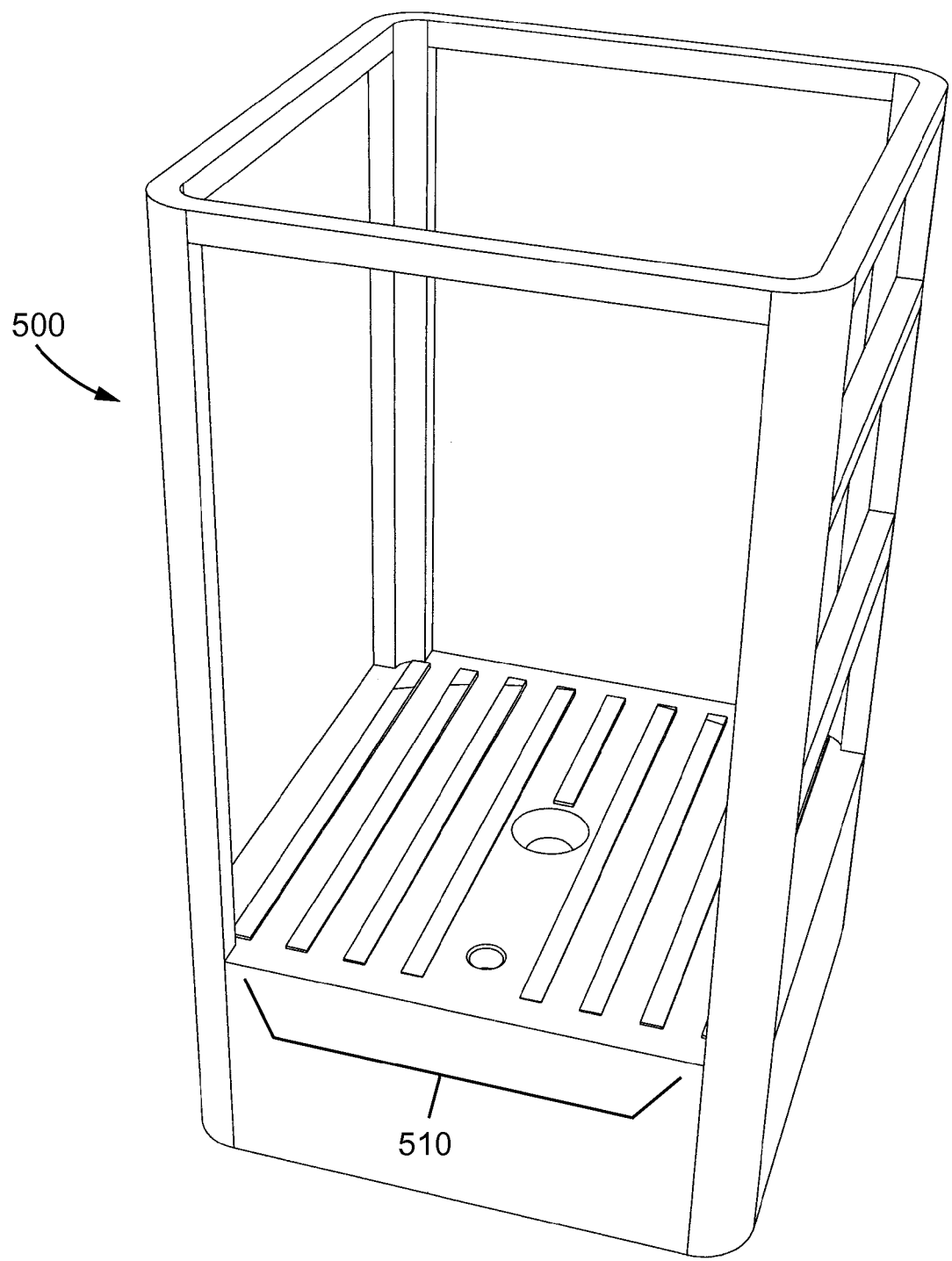
FIG. 4 is a view of a tote including contour strips, such that, when the support is placed in the tote (over the contour strips), the base plate has a horizontal axis providing a high point and a low point, the low point being located at the offset second opening.

The support is preferably loaded into the tote such that, the base plate, when placed in the tote, has a horizontal axis providing a high point and a low point, the low point being located at the offset second opening, for improved drainage of the biocontainer bag. As shown in FIG. 4, the tote 500 (tote baffles not shown) can include angled "contour strips" 510 (e.g., thinner near the offset second opening, thicker near the first opening) such that, when the support is loaded in the tote, the low point is located at the offset second opening. Alternatively, the bottom of the base plate of the support can include the contour strips (not shown). The desired angle between high and low points can be selected as is known in the art.

Once bioprocessing has been completed, the biocontainer bag can be removed from the tote, transported to the desired location, and removed from the support after the sidewalls and front wall of the support are unlocked and unfolded.

While embodiments of the invention are suitable for use with a wide variety of biocontainers and biocontainer sets including tubing, they are especially suitable for a biocontainer tube management system comprising the biocontainer bag, tubing, and a tube support. For example, FIG. 8 shows an illustrative biocontainer tube management system 2000 comprising a flexible biocontainer bag 100 containing an impeller 800, the bag comprising a top wall 101, a bottom wall 102, and opposing side walls 103, 104, 105, 106, providing an interior volume therein; a tube support 200 comprising a plate 210 including tabs 211A, 211B, 212A, and 212B, as well as a plurality of slots 215A, wherein the tube support is attached to a wall (shown attached to sidewall 106) of the bag; and, a plurality of hollow tubes 216B attached to the bag and in fluid communication with the interior volume of the bag, wherein the tubes are retained in the slots of the tube support.

Figure 9:
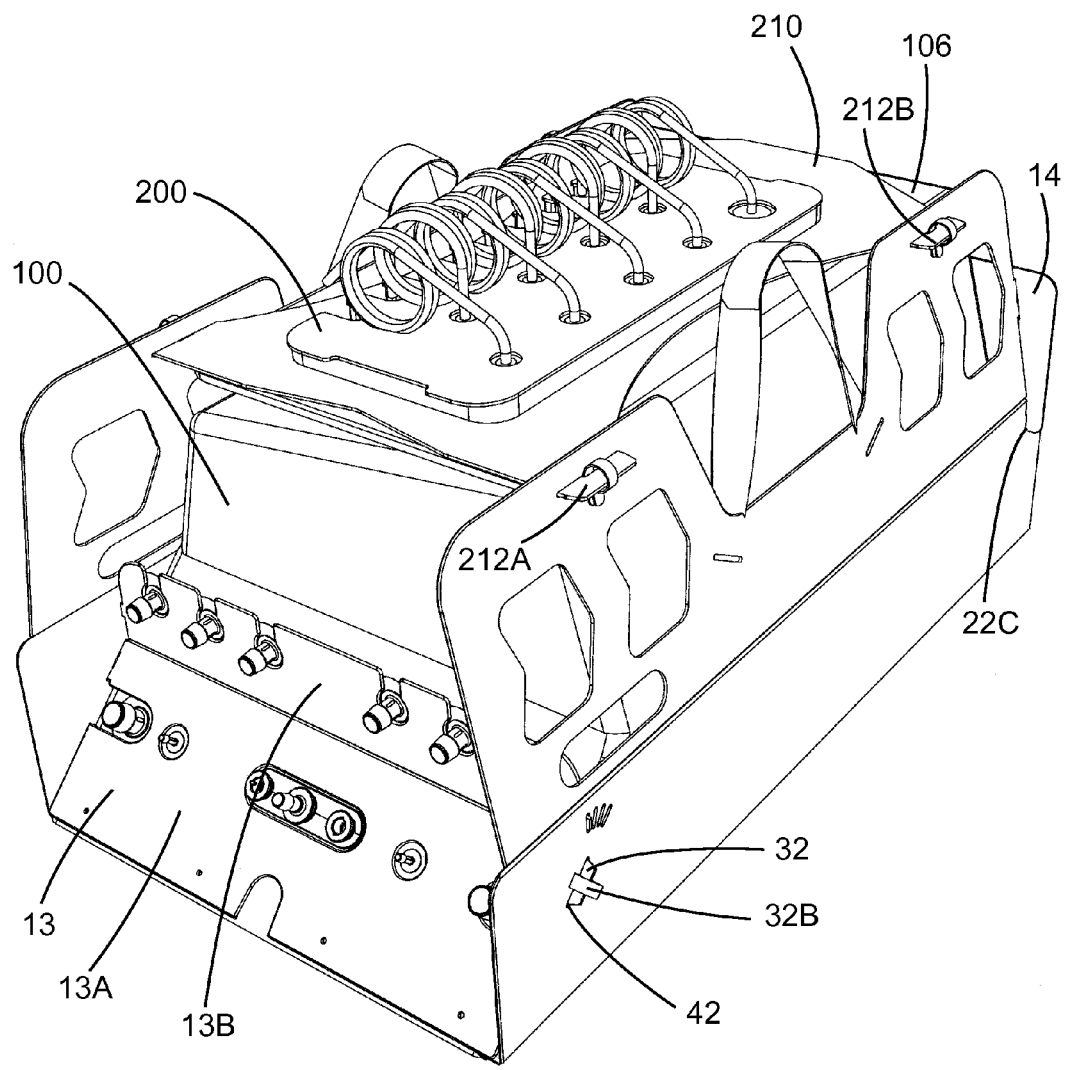
FIG. 9 is a front top perspective view of an assembled support containing the biocontainer tube management system shown in FIG. 8.
Figure 10:
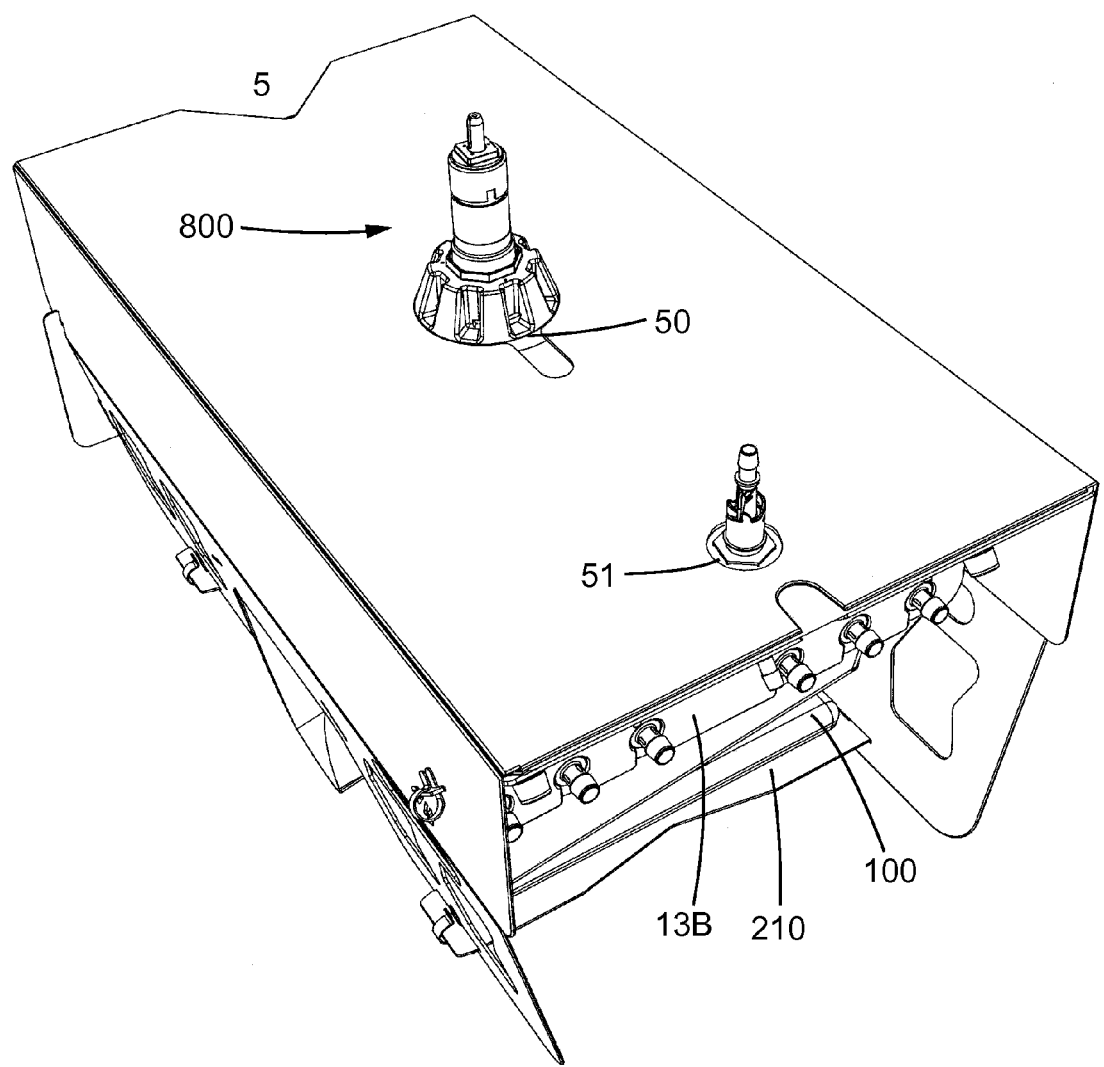
FIG. 10 is a bottom perspective view of an assembled support containing the biocontainer tube management system shown in FIG. 8, also showing the lower portion of the impeller housing assembly, and the drain port of the biocontainer bag, projecting through the first and second openings in the base plate of the support.

Using FIGS. 5-7 and 9 for reference (wherein the FIGS. 5-7 only show plate 210 without the rest of the biocontainer tube management system, and FIG. 9 shows a biocontainer tube management system with the plate 210), tabs 211A, 211B, 212A, and 212B can be engaged with respective sidewall slots 221A, 221B, 222A, and 222B, and if desired, and the tabs can include slots similar to those described with respect to tabs 31, 32, 21 and 22 as described above, e.g., for allowing retainers to be placed in the slots to more securely (but temporarily, if desired), lock the sidewalls and plate together. The biocontainer tube management system can be transported as described above.

The biocontainer bag can have any suitable number and locations of additional ports, for example, one or more of any of the following ports: a liquid inlet port, a gas inlet port, a gas outlet port, a powder inlet port, an acid/base inlet port, a probe port, a sample port, and/or a probe support port. For example, the biocontainer bag 100 shown in FIGS. 9 and 10 includes a plurality of ports. A variety of fluids can be processed and/or prepared (including mixing) in accordance with biocontainer bags. Applications include, for example, cell culture (e.g., including batch and fed-batch operations of suspension and adherent cell lines), preparing sterile fluids for the pharmaceutical and/or biopharmaceutical industries, including drugs, vaccines, and intravenous fluids, antibody- and/or protein-containing fluids, and/or fluids for the food and beverage industry. Fluids mixed according to embodiments of the invention can also used, for example, as media and/or buffers such as chromatography buffers.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A support for a biocontainer bag including an impeller to be placed in a tote comprising:
   (a) a base plate having opposing sides, a bottom, a front end and a rear end, and including a generally centrally located first opening; and an offset second opening located near the front end; the first opening having a first diameter; the offset second opening having a second diameter, the second diameter being less than the first diameter; the base plate further comprising a notch at the rear end, wherein the notch allows alignment with a tote; wherein the base plate bottom has angled contoured strips such that, when the base plate is placed in the tote, the base plate has a high point and a low point, the low point being located at the offset second opening;

(b) first and second opposing side walls, hingedly connected to respective opposing sides of the base plate, each side wall having an upper portion and a lower portion, and a horizontally arranged hinge between the upper portion and the lower portion, and including at least one opening suitable for grasping the side wall and/or including a strap for carrying the support while transporting the biocontainer bag to and/or from the tote; and, (c) a front wall, hingedly connected to the front end of the base plate, the front wall having an upper portion and a lower portion, and a horizontally arranged hinge between the upper portion and the lower portion, wherein the front wall has tabs including retainer slots, and the side walls each have a receiving slot, wherein the tabs on the front wall are insertable into the receiving slots to engage the front wall and side walls together in place; the support further comprising retainers placeable in the retainer slots, allowing the front wall to be temporarily locked to the side walls after the tabs on the front walls are inserted into the receiving slots.

2. The support of claim 1, wherein the front wall has a plurality of slots and/or openings for accommodating biocontainer bag tubing, probe supports, and/or ports.

3. The support of claim 1, wherein the side walls and/or the front wall are attached to the base plate as an integral structure.

4. The support of claim 1, further comprising first and second straps, respectively attached to the first and second opposing side walls.

5. The support of claim 1, for supporting a biocontainer tube management system comprising the biocontainer bag and a tube support, wherein the upper portions of each of the first and second opposing side walls each include at least two slots for engaging the tube support.

6. The support of claim 1, wherein the side walls each include at least one chevron-shaped opening providing a directional indication to an operator for loading the biocontainer bag into the tote.

7. The support of claim 6, wherein the side walls each include tabs including retainer slots, and the support further comprises a rear wall including slots, wherein the tabs on the side walls are insertable into the slots in the rear wall to engage the rear wall and side walls together in place; the support further comprising retainers placeable in the retainer slots, allowing the rear wall to be temporarily locked to the side walls after the tabs on the side walls are inserted into the receiving slots.

8. The support of claim 1, wherein the side walls each include tabs including retainer slots, and the support further comprises a rear wall including slots, wherein the tabs on the side walls are insertable into the slots in the rear wall to engage the rear wall and side walls together in place; the support further comprising retainers placeable in the retainer slots, allowing the rear wall to be temporarily locked to the side walls after the tabs on the side walls are inserted into the receiving slots.

9. A method for transporting a biocontainer bag including an impeller, the method comprising placing the biocontainer bag on a base plate of a support, the support comprising (a) the base plate, wherein the base plate has opposing sides, a bottom, a front end and a rear end, and including a generally centrally located first opening; and an offset second opening located near the front end; the first opening having a first diameter; the offset second opening having a second diameter, the second diameter being less than the first diameter; the base plate further comprising a notch at the rear end, wherein the notch allows alignment with a tote; wherein the base plate bottom has angled contoured strips such that, when the base plate is placed in the tote, the base plate has a high point and a low point, the low point being located at the offset second opening;

(b) first and second opposing side walls, hingedly connected to respective opposing sides of the base plate, each side wall having an upper portion and a lower portion, and a horizontally arranged hinge between the upper portion and the lower portion, and including at least one opening suitable for grasping the side wall and/or including a strap for carrying the support while transporting the biocontainer bag to and/or from the tote; and, (c) a front wall, hingedly connected to the front end of the base plate, the front wall having an upper portion and a lower portion, and a horizontally arranged hinge between the upper portion and the lower portion, wherein the front wall has tabs including retainer slots, and the side walls each have a receiving slot, wherein the tabs on the front wall are insertable into the receiving slots to engage the front wall and side walls together in place; the support further comprising retainers placeable in the retainer slots, allowing the front wall to be temporarily locked to the side walls after the tabs on the front walls are inserted into the receiving slots;

moving at least the lower portions of the first and second opposing walls to substantially vertical positions, inserting the tabs on the front walls into the receiving slots; placing retainers in the retainer slots, and transporting the biocontainer to a desired location.

10. The method of claim 9, including moving the upper portions inwardly via the horizontally arranged hinge.

11. The method of claim 9, further comprising, before transporting the biocontainer bag to a desired location, inserting the tabs on the front wall into the receiving slots of the side walls, and temporarily locking the front wall and side walls together.

12. The method of claim 9, further comprising placing the support in the tote, wherein a baffle of the tote is located in the notch in the base plate.

* * * * *